US00PP35255P2

(12) United States Plant Patent
van Sambeek

(10) Patent No.: US PP35,255 P2
(45) Date of Patent: Jul. 4, 2023

(54) ***AGASTACHE* PLANT NAMED 'DOAGABETAMBER'**

(50) Latin Name: *Agastache aurantiaca*
Varietal Denomination: Doagabetamber

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/991,457

(22) Filed: Nov. 21, 2022

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./399
CPC ..... A01H 6/50; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Agastache* plant named 'Doagabetamber', characterized by its relatively compact and upright to outwardly spreading plant habit; moderately vigorous growth habit and moderate growth rate; medium green-colored leaves; relatively compact inflorescences with numerous bright orange-colored flowers; and good garden performance.

2 Drawing Sheets

Figure 1:
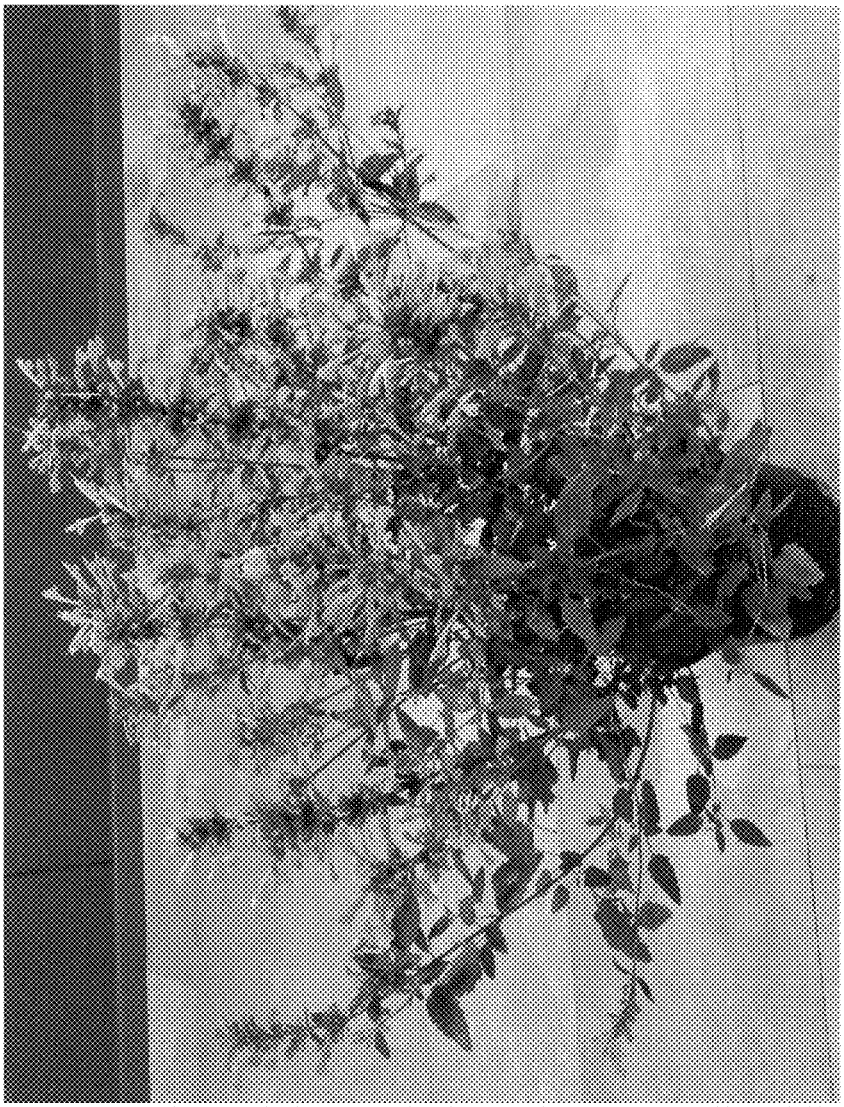

Botanical designation: *Agastache aurantiaca.*
Cultivar denomination: 'DOAGABETAMBER'.

BACKGROUND OF THE INVENTION

The present invention relates to a new and distinct cultivar of *Agastache* plant, botanically known as *Agastache aurantiaca*, commonly referred to as Giant Hyssop or Hummingbird Mint and hereinafter referred to by the name 'Doagabetamber'.

The new *Agastache* plant is a product of a planned breeding program conducted by the Inventor in Aalsmeer, The Netherlands. The objective of the breeding program is to create new and unique *Agastache* plants.

The new *Agastache* plant originated from a cross-pollination in Aalsmeer, The Netherlands in July, 2017 of *Agastache aurantiaca* 'Kudos Gold', disclosed in U.S. Patent Application Publication number 2015/0334904, as the female, or seed, parent with a proprietary selection of *Agastache aurantiaca* identified as code number MP-0016, not patented, as the male, or pollen, parent. The new *Agastache* plant was discovered and selected by the Inventor as a single flowering plant from within the progeny of the stated cross-pollination in a controlled environment in Aalsmeer, The Netherlands in July, 2018.

Asexual reproduction of the new cultivar by vegetative cuttings in a controlled environment in Aalsmeer, The Netherlands since August, 2018 has shown that the unique features of this new *Agastache* plant are stable and reproduced true to type in successive generations.

SUMMARY OF THE INVENTION

Plants of the new *Agastache* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doagabetamber'. These characteristics in combination distinguish 'Doagabetamber' as a new and distinct *Agastache* plant:

1. Relatively compact and upright to outwardly spreading plant habit.
2. Moderately vigorous growth habit and moderate growth rate.
3. Medium green-colored leaves.
4. Relatively compact inflorescences with numerous bright orange-colored flowers.
5. Good garden performance.

Plants of the new *Agastache* can be compared to plants of the female parent, 'Kudos Gold'. Plants of the new *Agastache* differ primarily from plants of 'Kudos Gold' in the following characteristics:

1. Plants of the new *Agastache* are shorter and more compact than plants of 'Kudos Gold'.
2. Plants of the new *Agastache* are not as vigorous as plants of 'Kudos Gold'.
3. Flowers of plants of the new *Agastache* are bright orange in color whereas flowers of plants of 'Kudos Gold' are dark yellow in color.

Plants of the new *Agastache* can be compared to plants of the male parent selection. Plants of the new *Agastache* differ primarily from plants of the male parent selection in the following characteristics:

1. Plants of the new *Agastache* are taller than plants of the male parent selection.
2. Flowers of plants of the new *Agastache* are bright orange in color whereas flowers of plants of the male parent selection are light yellow in color.

Plants of the new *Agastache* can be compared to plants of *Agastache aurantiaca* 'Kudos Ambrosia', disclosed in U.S. Patent Application Publication number 2014/0373234. In side-by-side comparisons, plants of the new *Agastache* differ primarily from plants of 'Kudos Ambrosia' in flower color as plants of the new *Agastache* have bright orange-colored flowers whereas plants of 'Kudos Ambrosia' have pink-colored flowers.

BRIEF DESCRIPTION OF THE PHOTOGRAPHS

The accompanying colored photographs illustrate the overall appearance of the new *Agastache* plant showing the colors as true as it is reasonably possible to obtain in colored reproductions of this type. Colors in the photographs may differ slightly from the color values cited in the detailed botanical description which accurately describe the actual colors of the new *Agastache* plant.

The photograph on the first sheet (FIG. 1) is a side perspective view of a typical flowering plant of 'Doagabetamber' grown in a container.

Figure 2:
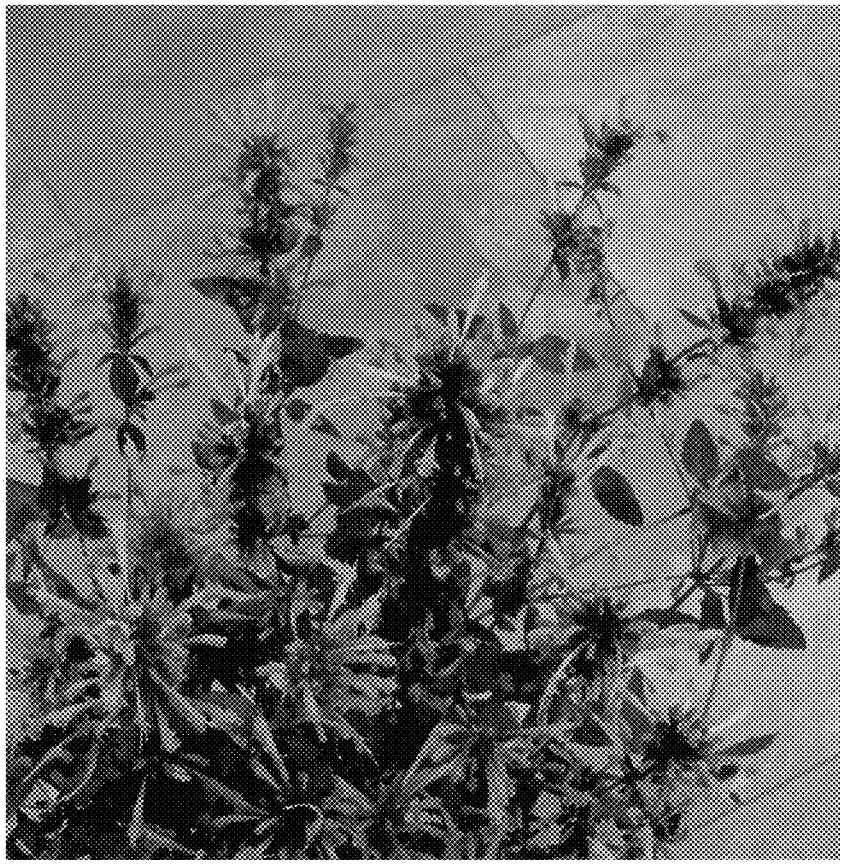

The photograph on the second sheet (FIG. 2) is a close-up view of a typical flowering plant of 'Doagabetamber'.

DETAILED BOTANICAL DESCRIPTION

The aforementioned photographs and following observations and measurements describe plants grown during the summer in 17-cm containers in a glass-covered greenhouse in Aalsmeer, The Netherlands and under conditions and cultural practices which approximate those typically used in commercial *Agastache* plant production. During the production of the plants, day temperatures averaged 21° C. and night temperatures averaged 15° C. Rooted young plants were pinched one week after planting and plants were 16 weeks old when the photographs were taken and 22 weeks old when the description was taken. In the following description, color references are made to The Royal Horticultural Society Colour Chart, Fifth Edition, except where general terms of ordinary dictionary significance are used.

Botanical classification: *Agastache aurantiaca* 'Doagabetamber'.

Parentage:

- *Female, or seed, parent.*—*Agastache aurantiaca* 'Kudos Gold', disclosed in U.S. Patent Application Publication number 2015/0334904.
- *Male, or pollen, parent.*—Proprietary selection of *Agastache aurantiaca* identified as code number MP-0016, not patented.

Propagation:

- *Type.*—By vegetative cuttings.
- *Time to initiate roots, summer.*—About 16 days at temperatures about 26° C.
- *Time to initiate roots, winter.*—About 21 days at temperatures about 23° C.
- *Time to produce a rooted young plant, summer.*—About 24 days at temperatures about 23° C.
- *Time to produce a rooted young plant, winter.*—About 28 days at temperatures about 18° C.
- *Root description.*—Thick and fibrous; typically white in color, actual color of the roots is dependent on substrate composition, water quality, fertilizer type and formulation, substrate temperature and physiological age of roots.
- *Rooting habit.*—Moderately freely branching; medium density.

Plant description:

- *Plant and growth habit.*—Herbaceous perennial typically grown as a container and garden plant; relatively compact and upright to somewhat outwardly spreading plant habit; moderately vigorous growth habit and moderate growth rate.
- *Branching habit.*—Freely basal branching with about 15 primary lateral branches each with up to eight secondary branches developing per plant; pinching enhances lateral branch development.
- *Plant height, soil level to top of foliar plane.*—About 42 cm.
- *Plant height, soil level to top of floral plane.*—About 42 cm.
- *Plant width.*—About 58 cm.
- *Primary branch description.*—Length (excluding inflorescence): About 44 cm. Diameter: About 3 mm. Internode length: About 6 cm. Shape: Quadrangular. Strength: Strong. Aspect: Erect to about 70° from vertical. Texture and luster: Smooth, glabrous; glossy. Color, developing: Close to 144B. Color, developed: Close to 143A.

Leaf description:

- *Arrangement.*—Opposite and decussate; simple.
- *Length.*—About 4.3 cm.
- *Width.*—About 3 cm.
- *Shape.*—Deltoid with ovate tendencies.
- *Apex.*—Acute.
- *Base.*—Truncate.
- *Margin.*—Crenate with medium indentations.
- *Texture and luster, upper and lower surfaces.*—Smooth, glabrous; matte.
- *Venation pattern.*—Pinnate and reticulate.
- *Color.*—Developing and fully expanded leaves, upper surface: Close to 137B; venation, close to 137B. Developing and fully expanded leaves, lower surface: Close to 138B; venation, close to 138B.
- *Petioles.*—Length: About 2.4 cm. Diameter: About 2 mm. Strength: Moderately strong; flexible. Texture and luster, upper and lower surfaces: Smooth, glabrous; glossy. Color, upper surface: Close to 143B. Color, lower surface: Close to 143C.

Flower description:

- *Flower arrangement and shape.*—Single bilabiate flowers arranged on erect and relatively compact spikes; freely flowering habit with about twelve flowers developing per inflorescence and about 940 flowers developing per plant during the flowering season; flowers face mostly outwardly.
- *Fragrance.*—Strongly fragrant; sweet.
- *Natural flowering season.*—Early flowering habit, plants begin flowering about 16 weeks after planting; plants flower from July to September in an outdoor environment in The Netherlands; flowers not persistent.
- *Flower buds.*—Length: About 2.1 cm. Diameter: About 5 mm. Shape: Elongated tubular. Texture and luster: Smooth, glabrous; glossy. Color: Close to 28A.
- *Inflorescence height.*—About 12 cm.
- *Inflorescence diameter.*—About 5 cm.
- *Flower size.*—About 6 mm by 8 mm.
- *Flower depth.*—About 3.2 cm.
- *Flower throat diameter.*—About 4 mm.
- *Flower tube length.*—About 2.5 cm.
- *Flower tube diameter, proximally.*—About 2 mm.

*Petals*.—Arrangement: Five petals; two upper petals (upper lip) with two lateral petals and one lower petal (lower lip); petals fused. Length, lobe: About 4 mm. Width, lobe: About 3 mm. Shape, lobe: Roughly spatulate. Apex, lobe: Obtuse. Texture and luster, upper surface: Smooth, glabrous; matte. Texture and luster, lower surface: Smooth, glabrous; glossy. Texture and luster, throat: Smooth, glabrous; matte. Texture and luster, tube: Smooth, glabrous; glossy. Color: When opening, upper and lower surfaces: Close to 28B. Fully opened, upper and lower surfaces: Close to 28B; venation, close to 28B; color not changing with subsequent development. Throat: Close to 28B; venation, close to 28B. Tube: Close to 28B; venation, close to 28B.

*Calyx*.—Arrangement: Five sepals fused to form a tubular calyx. Length: About 6 mm. Width: About 3 mm. Sepal length: About 6 mm. Sepal width: About 1 mm. Sepal shape: Roughtly obovate; fused. Sepal apex: Acuminate. Sepal margin: Entire. Sepal texture and luster, upper surface: Smooth, glabrous; semi-glossy. Sepal texture and luster, lower surface: Smooth, glabrous; glossy. Sepal color: When opening, upper and lower surfaces: Close to 185C and 144A. Fully opened, upper and lower surfaces: Close to 185C and 144A.

*Pedicels*.—Length: About 3 mm. Diameter: About 0.5 mm. Strength: Moderately weak. Aspect: About 5° from peduncle axis. Texture and luster: Smooth, glabrous; glossy. Color: Close to 185C and 144A.

*Reproductive organs*.—Stamens: Quantity per flower: Four. Filament length: About 1.4 cm. Filament color: Close to 28B. Anther shape: Rounded; basifixed. Anther size: About 1 mm by 1 mm. Anther color: Close to 77A. Pollen amount: Abundant. Pollen color: Close to 155D. Pistils: Quantity per flower: One. Pistil length: About 2.3 cm. Stigma diameter: About 0.1 mm. Stigma shape: Cleft. Stigma color: Close to 145B. Style length: About 2.1 cm. Style color: Close to 155D. Ovary color: Close to 151A.

*Seeds and fruits*.—To date, seed and fruit production has not been observed on plants of the new *Agastache*.

Pathogen & pest resistance: To date, plants of the new *Agastache* have not been noted to be resistant to pathogens and pests common to *Agastache* plants.

Garden performance: Plants of the new *Agastache* have exhibited good garden performance, to tolerate temperatures ranging from −20° C. to about 35° C. and to be suitable for USDA Hardiness Zone 6.

It is claimed:

1. A new and distinct *Agastache* plant named 'Doagabetamber' as illustrated and described.

* * * * *